(12) United States Patent
Cheng et al.

(10) Patent No.: US 9,814,445 B2
(45) Date of Patent: *Nov. 14, 2017

(54) ULTRASONIC DIAGNOSTIC IMAGING SYSTEM WITH CONTEXTUALLY VARIABLE CONTROL PANEL

(71) Applicant: KONINKLIJKE PHILIPS N.V., Eindhoven (NL)

(72) Inventors: Jeanne Cheng, Andover, MA (US); Zsolt Mark, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/359,677

(22) Filed: Nov. 23, 2016

(65) Prior Publication Data

US 2017/0071572 A1    Mar. 16, 2017

Related U.S. Application Data

(63) Continuation of application No. 14/241,175, filed as application No. PCT/IB2012/055018 on Sep. 21, 2012, now Pat. No. 9,504,448.

(Continued)

(51) Int. Cl.
*A61B 8/00* (2006.01)
*A61B 8/08* (2006.01)
*G06F 3/0489* (2013.01)
*A61B 8/14* (2006.01)
*G06F 3/044* (2006.01)

(52) U.S. Cl.
CPC ............... *A61B 8/465* (2013.01); *A61B 8/14* (2013.01); *A61B 8/4405* (2013.01);
(Continued)

(58) Field of Classification Search
CPC .......... A61B 8/465; A61B 8/14; A61B 8/463; A61B 8/4405; A61B 8/4433; A61B 8/486;
(Continued)

(56) References Cited

U.S. PATENT DOCUMENTS 5,997,479 A   12/1999   Savord et al.
6,063,030 A   5/2000    Vara et al.
(Continued)

FOREIGN PATENT DOCUMENTS

EP   1925257 A1   5/2008
EP   2337225 A1   6/2011

*Primary Examiner* — Sanjay Cattungal (57) ABSTRACT

An ultrasound system has a control panel formed of a top glass plate with control area graphics screened onto the bottom surface of the glass plate. Capacitive foils are attached to the areas of the screened graphics, enabling a user control to be capacitively selected by touching the top surface above the screened graphics. Each control area is selectively back-illuminated by a diffuser frame with light pipes fastened below the glass plate. LEDs for illumination are mounted on a printed circuit board fastened to the diffuser frame, which are controlled by the printed circuit board. Different groups of user controls are illuminated in accordance with the context of the operating mode or imaging procedure being performed so that only needed control are illuminated while unneeded controls are invisible to the user. All of the controls can be extinguished and de-activated so that the top surface of the control panel can be cleaned without randomly activating the controls of the control panel.

15 Claims, 6 Drawing Sheets

Related U.S. Application Data

(60) Provisional application No. 61/540,586, filed on Sep. 29, 2011.

(52) U.S. Cl.
CPC ............ *A61B 8/4433* (2013.01); *A61B 8/462* (2013.01); *A61B 8/463* (2013.01); *A61B 8/466* (2013.01); *A61B 8/467* (2013.01); *A61B 8/486* (2013.01); *A61B 8/488* (2013.01); *A61B 8/54* (2013.01); *G06F 3/044* (2013.01); *G06F 3/04895* (2013.01); *A61B 8/4477* (2013.01); *A61B 8/483* (2013.01)

(58) Field of Classification Search
CPC ........... A61B 8/488; A61B 8/467; A61B 8/54; A61B 8/466; A61B 8/462; A61B 8/4477; A61B 8/483; G06F 3/044; G06F 3/04895
USPC .................................................. 600/437–469
See application file for complete search history.

(56) References Cited

U.S. PATENT DOCUMENTS

| | | |
|---|---|---|
| 6,436,048 B1 | 8/2002 | Pesque |
| 2008/0009728 A1 | 1/2008 | Malchow |
| 2008/0119731 A1 | 5/2008 | Becerra |
| 2008/0125655 A1 | 5/2008 | Song |
| 2008/0281195 A1 | 11/2008 | Heimdal |
| 2008/0281196 A1 | 11/2008 | Sornes |
| 2009/0131793 A1 | 5/2009 | Stonefield et al. |
| 2009/0262085 A1 | 10/2009 | Wassingbo et al. |
| 2010/0007610 A1 | 1/2010 | Shin |
| 2010/0049046 A1 | 2/2010 | Peiffer |

ULTRASONIC DIAGNOSTIC IMAGING SYSTEM WITH CONTEXTUALLY VARIABLE CONTROL PANEL

The present application is a continuation of U.S. patent application Ser. No. 14/241,175 filed Feb. 26, 2014, which is the U.S. National Phase application under 35 U.S.C. §371 of International Application No. PCT/IB2012/055018, filed Sep. 21, 2012, which claims the benefit of U.S. Provisional Application Ser. No. 61/540,586 filed Sep. 29, 2011. These applications are hereby incorporated by reference herein.

This invention relates to medical diagnostic ultrasonic imaging systems and, in particular, to ultrasound systems with control panels with controls which vary with the type of diagnostic procedure being performed.

Medical diagnostic ultrasound system have control panels with many user controls for setting up and controlling the system to perform the desired imaging exam. Starting from a number of preset control parameters for a desired exam, the operator will manipulate the controls to vary the settings to those uniquely suited for the particular exam to be performed. Once the starting control parameters have been established, the exam can begin and the same and additional controls are manipulated to vary the performance of the system as the exam proceeds. For example, the operator can set the imaging mode for B mode, Doppler, or M mode. The size and angle of the image field can be changed and the frequency adjusted for fundamental or harmonic imaging. The system gain can be adjusted to more clearly distinguish anatomy at deeper depths in the body, and time gain control slides are adjusted to provide the appropriate gain over the depth of interest. Focal zones can be added and repositioned to different depths. Additional modes can be added during the exam, such as a spectral Doppler display when a Doppler gate is placed over the anatomy. A wide variety of measurements can be made of the anatomy and blood flow parameters estimated. These are but a few of the controls and adjustments available on a typical ultrasound system control panel.

While every ultrasound exam can require the adjustment and use of many controls on the control panel, different types of exams can require the use of a slightly different or significantly different group of controls. Thus, the control panel must contain a very large number of user controls to accommodate all the variable uses and functions of the ultrasound system. The ever-increasing number of controls has been addressed by different equipment providers in different ways. Some simply increase the number and/or density of mechanical controls on the control panel. Others augment the mechanical controls with softkey controls on the system display screen, which the user can call up and adjust and click with a computer mouse or trackball control on the control panel. Still others have employed softkey controls on a touchpanel display, which the user can manipulate and adjust manually without the need for a computer pointing device. The iU33 echocardiography system, available from Philips Healthcare of Andover, Mass. has all three: a fully populated mechanical control panel, softkeys on the system display screen and small touchpanels for additional user controls.

One approach to dealing with the large number and varying variety of controls needed for an ultrasound system is described in U.S. Pat. No. 6,063,030 (Vara et al.) This patent describes a virtual control interface for an ultrasound system in which the entire control interface is comprised of softkeys. A major portion of the display screen is devoted to the ultrasound image and a panel on the side of the screen is filled with controls which adapt to the type of and stage of an imaging exam. At the outset of the exam the side panel contains setup controls. Once the exam is underway the side panel display changes and contains controls appropriate for the type of exam. At different phases of the exam the side panel display is changed to provide controls appropriate for the particular phase of the exam. When measurements are to be made on the image, for instance, the side panel changes to display measurement controls. The user can also call up specific control sets when needed. If the user wants to annotate body markers on an anatomical model, for example, the body marker display and control panel is called up and the user annotates the graphical model, which is then saved with the results of the exam.

It is possible, though, for a user to become lost in the ever-changing panoply of virtual controls. A simpler, more intuitive approach to control configuration is often preferable. Moreover, some user controls are frequently used, whereas others are only needed in specific circumstances. It is further desirable for the user to have more commonly used controls readily at hand, but with the ability to call upon more specialized controls when needed. In addition, the commonly used controls should be in unvarying locations so the user can intuitively access them without having to hunt for their currently placement and location. Furthermore, these objectives should also include providing the controls needed for a particular exam while unneeded controls are removed from the user's access.

In accordance with the principles of the present invention an ultrasound system user control panel is provided in which the user controls needed for a particular ultrasound exam are available for use and unneeded controls are hidden from the user and neither available nor distractive to the user. The user controls on the control panel are in fixed physical locations on the control panel so that the user will always find a given control at the same place on the panel. In a constructed embodiment available user controls are illuminated and visible to the user and controls not necessary in the context of a current exam are darkened and invisible. All of the controls are touch actuated and located beneath a continuous surface, a dark glass plate, so that there are no crevices or projections to trap dust and acoustic gel. The continuous surface enables the control panel to be easily cleaned for patient and operator health and safety. The controls can all be turned off by a switch while the ultrasound system is still powered on, in which case none will be accidentally actuated when the control panel surface is being cleaned.

Figure 1:
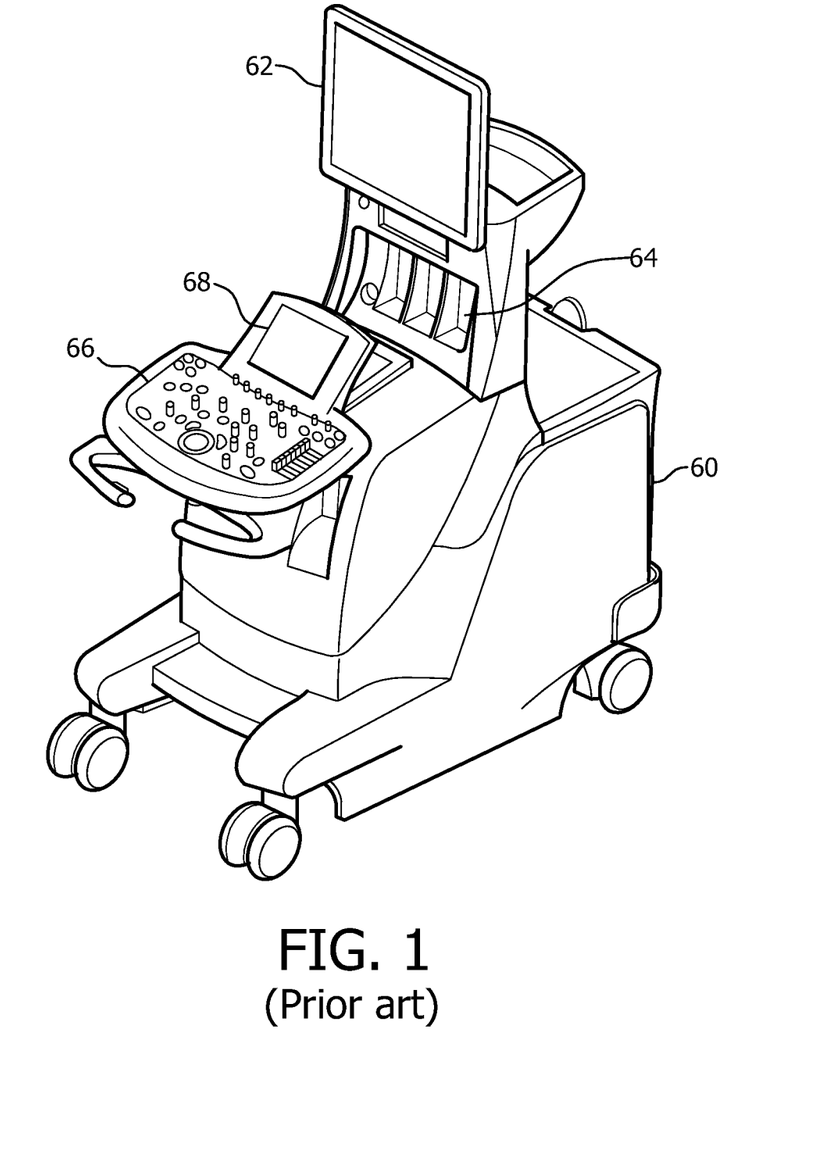
FIG. 1 illustrates a cart-borne ultrasound system of the prior art.

Referring first to FIG. 1, a typical cart-borne ultrasound system of the prior art is shown. The ultrasound system includes a mainframe or chassis 60 containing most of the electronic circuitry for the system. The chassis 60 is wheel-mounted so that it can be rolled to the location in a hospital or clinic where it is to be used. An image display 62 is mounted on the chassis 60. A variety of imaging probes may be plugged into three connectors 64 on the chassis. Mounted at the front of the chassis 60 is a control panel 66 with a keyboard and controls arrayed over the surface of the control panel, by which a sonographer operates the ultrasound system and enters information about the patient or the type of examination that is being conducted. At the back of the control panel 36 of the illustrated ultrasound system is a touchscreen display 68 on which programmable softkeys are displayed for specific control functions. The sonographer selects a softkey on the touchscreen display 18 simply by touching the image of the softkey on the display. At the bottom of the touchscreen display is a row of control knobs, the functionality of which varies in accordance with the softkey labels on the touchscreen immediately above each button. At the front of the control panel is a trackball which the sonographer manipulates to indicate anatomy of the ultrasound image on the image display 62, and to steer a pointer or cursor on the screen to indicate a softkey on the display screen, which is selected by clicking a button adjacent to the trackball. Above and around the trackball are a variety of switches, buttons, and knobs which the sonographer manipulates to adjust the imaging parameters of the ultrasound system such as a signal gain knob, time gain control slide switches, and save and print buttons. The many knobs, buttons, and switches of the control panel make cleaning difficult, as dust and acoustic gel can easily become trapped around and under the controls.

Figure 2:
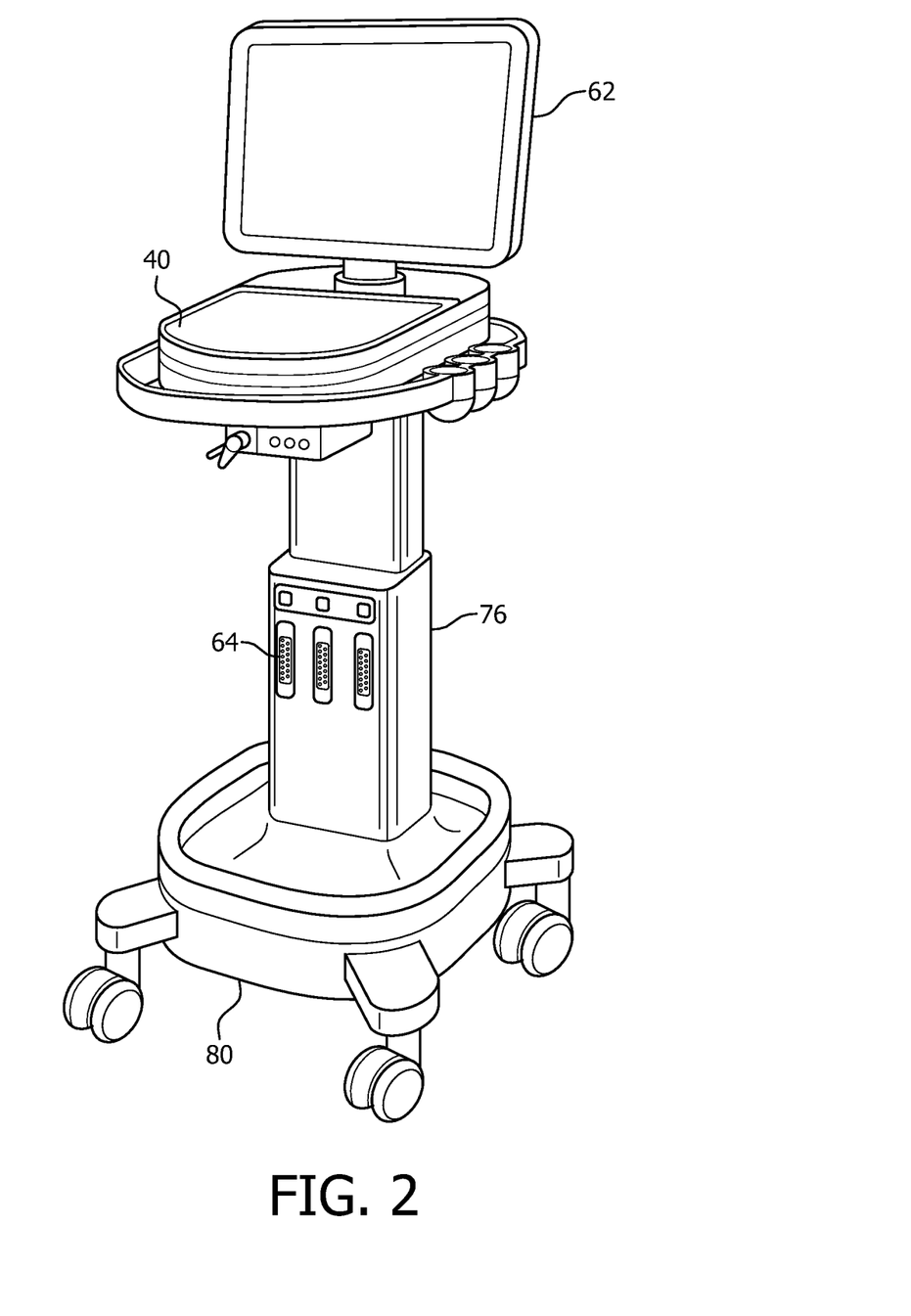
FIG. 2 illustrates a portable ultrasound system constructed in accordance with the principles of the present invention.

FIG. 2 illustrates a portable ultrasound system of the present invention. The electronics of the ultrasound system are located in a base 80 between the wheels of the system. A central column 76 supports the control panel 40 and the image display 62 at the top of the column. The upper portion of the column 76 may be configured to move up and down with respect to the lower portion of the column so that the height of the control panel and display screen may be adjusted. The connectors for three probes are located on the lower portion of the column. The control panel has no knobs, buttons, switches or other projections but has a continuous smooth dark planar surface of plastic or preferably glass. The flat, smooth glass surface of the control panel will not trap dust, gel or debris.

Figure 3:
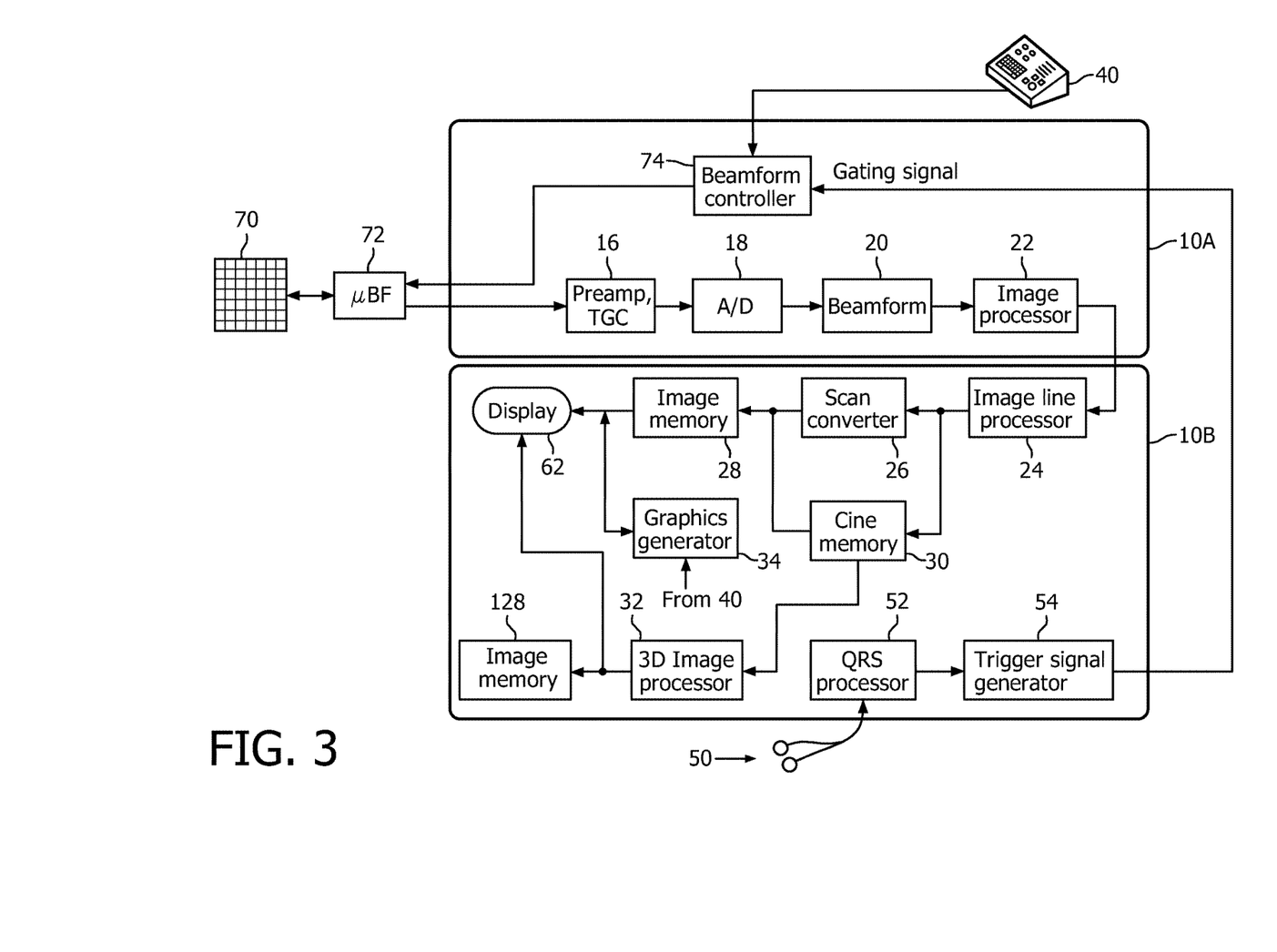
FIG. 3 is a block diagram of an ultrasound system constructed in accordance with the principles of the present invention.

A functional block diagram of the ultrasound system of FIG. 2 is illustrated in FIG. 3. The ultrasound system operates through two major subsystems, a front end acquisition subsystem 10A and a display subsystem 10B. An ultrasound probe is coupled to the acquisition subsystem to transmit ultrasound waves and receive ultrasound echo signals. The probe may do this with a linear (one-dimensional) row of transducer elements, or may use a two-dimensional matrix array of transducer elements 70 and a micro-beamformer 72 located in the probe. The micro-beamformer contains circuitry which controls the signals applied to groups of elements of the array transducer 70 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque), and provides electronic steering of beams on transmit and receive for high frame rate real-time (live) imaging.

The probe is coupled to the acquisition subsystem 10A of the ultrasound system. The acquisition subsystem includes a beamform controller 74 which is responsive to controls of the control panel 40 and provides control signals to the microbeamformer 72, instructing the probe as to the timing, frequency, direction and focusing of transmit and receive beams. The beamform controller also control the beamforming of echo signals received by the acquisition subsystem by its control of analog-to-digital (A/D) converters 18 and a beamformer 20. Partially beamformed echo signals received by the probe are amplified by preamplifier and TGC (time gain control) circuitry 16 in the acquisition subsystem, then digitized by the A/D converters 18. The digitized echo signals are formed into fully steered and focused beams by a main system beamformer 20. The echo signals are processed by an image processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format on the display screen 62. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The scan converter can thus format rectilinear or sector image formats. The image is then stored in an image memory 28 from which it can be displayed on the display 62. The image in memory is also overlaid with graphics to be displayed with the image, which are generated by a graphics generator 34 which is responsive to the user control 40 so that the graphics produced are associated with the images of the display. Individual images or image sequences can be stored in a cine memory 30 during capture of image loops or sequences. Images for diagnosis can be stored on a networked image memory 128.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 128 for storage of the 3D data sets for later review and diagnosis.

An ECG subsystem is provided for use when it is desirable to acquire images at particular phases of the heart cycle. ECG leads 50 provide ECG signals for a QRS processor 52 which identifies the R-wave of each heartbeat. The timing of the R-wave is used to acquire images of a particular heart cycle. Images of the heart at the end diastole phase of a succession of heartbeats can be acquired by coupling the R-wave timing as a trigger signal from a trigger signal generator 54 for the beamform controller 74 and the controls of the control panel 40 used to select the desired heart phase at which heart phase-gated images are to be acquired.

Figure 4:
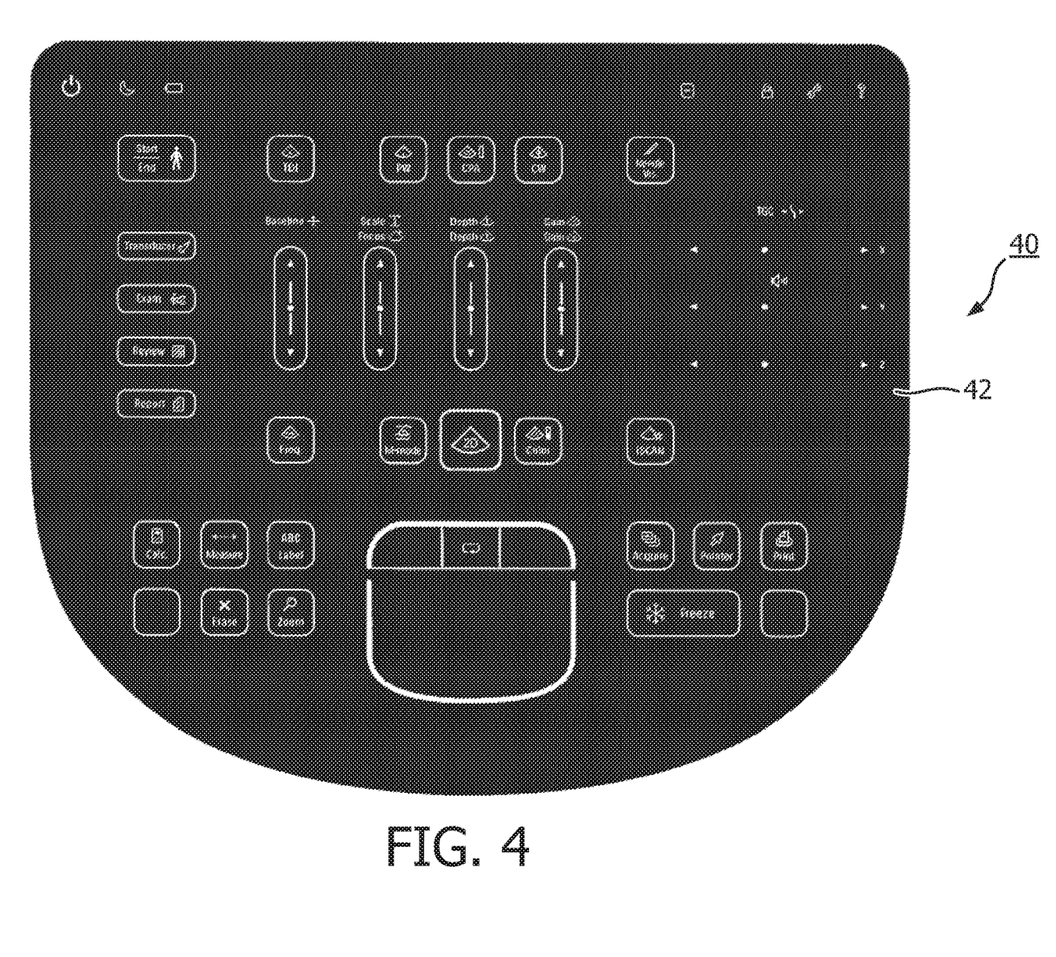
FIG. 4 illustrates a contextually variable ultrasound system control panel constructed in accordance with the principles of the present invention.

In accordance with the principles of the present invention, the ultrasound system of FIGS. 2 and 3 contains a context-variable control panel 40 as shown in FIGS. 4, 5, 6, and 6a. The upper layer of the control panel is a flat sheet of optically transparent material. The upper layer can be formed by a sheet of plastic or other polymer, but preferably is formed by a sheet of glass 42 so as to be more resistant to scratches and more impervious to solvents that may be found in a hospital. The glass sheet 42 presents a smooth, uniform surface on the top of the control panel. The underside 44 of the glass sheet 42 is painted a dark opaque color such as black or charcoal, except in locations where control graphics are screened on the back surface. The screening is a transparent or translucent color which outlines the individual control area as shown in FIG. 4. Within the control outline is text or a graphic symbol which identifies the function controlled by the specific control. The graphics may also be adjacent to a control as shown for the Baseline, Scale/Focus, Depth and Gain controls. Capacitive foils 46 are adhesively attached to the back of the screened glass which are sensitive to the touch of an operator on the glass above a particular foil. The touch by an operator on the area of a graphically-delineated control produces a capacitive change which is sensed by the underlying foil and coupled to the control panel electronics on a printed circuit board 82 below the glass sheet 42 and foils 46. Electrical conductors between the control areas connect individual foils to circuitry on the printed circuit board, which sends a control signal to the ultrasound system electronics in response to the sensing of a touch on a control area by the system operator.

Figures 6, 6A:
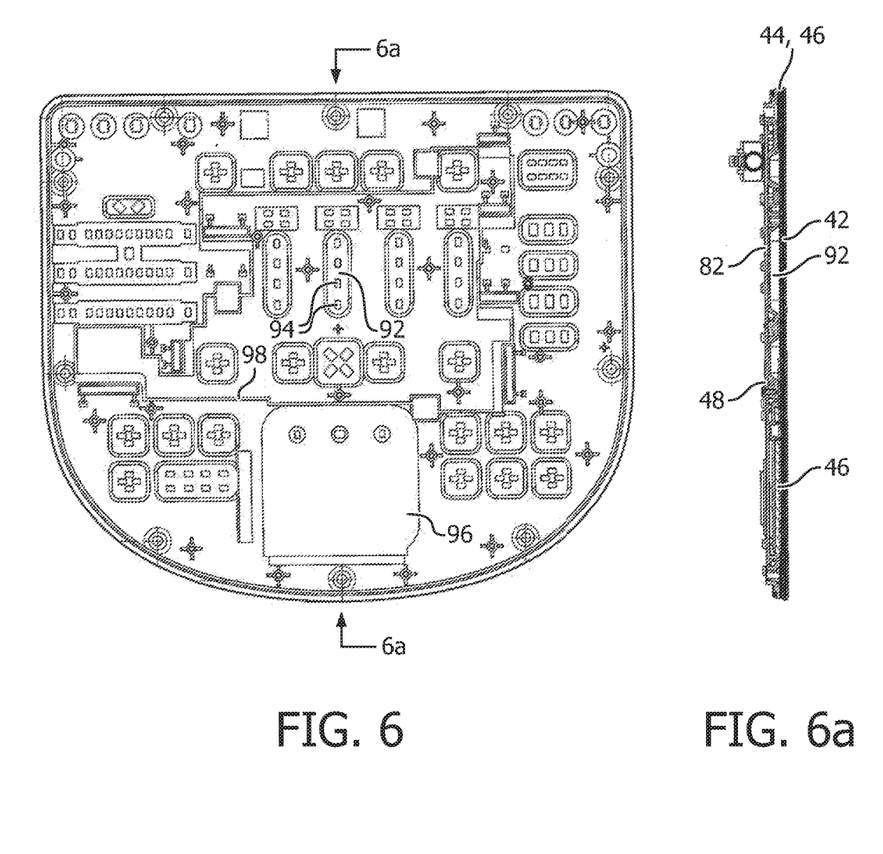
FIG. 6 is an internal view of the control panel of FIG. 4.
FIG. 6a is a cross-sectional view of the control panel of FIGS. 4-6.

The glass sheet with its screened graphics and capacitive foils is adhered to a white barrier layer 48 which in turn is fastened to the printed circuit board 82 on the other side of the white barrier layer. The white barrier layer 48 contains depressions or pockets such as 92 behind the areas of specific controls. Light sources such as LEDs 94 mounted on the underlying printed circuit board extend into these depressions or pockets from below and fill a pocket with light when the LED or LEDs in the pocket are illuminated. The surrounding area of the white barrier layer contacts the painted glass plate around each control area (or the capacitive foil layer laminated to the glass plate), confining the light of the LED in the depression (light chamber) to the area of the specific control. A depression in the barrier layer 48 thus forms a diffuser frame with light chambers which distribute the light of an LED over the graphics of a specific control and pipes the light to the control graphic, while the peripheral contact with the glass plate prevents the light from the specific control from bleeding into the area of an adjacent control. In a constructed embodiment the white barrier layer is not a unitary structure but is formed of sections which fit together with gaps 98 between the sections. The capacitive foils or foil conductors extend through these gaps to electrically connect to the underlying printed circuit board 82. Technologies suitable for constructing a control panel as described herein are available from RAFI GmbH & Co. KG, Ravensburg, Germany.

In a constructed example, the light chambers generally include multiple LED light sources of different colors. When a control is not to be used for a specific diagnostic procedure, none of the LEDs of the control area are illuminated and the light chamber is dark, causing the control to be virtually invisible to the ultrasound system operator. If the ultrasound system is not operating in the PW or CW mode, for example, the Baseline control slider is darkened and unavailable to the operator. The operator is thus presented with only those controls which are applicable to the current ultrasound system mode or procedure. In the constructed example, controls which are available in the current mode or procedure are illuminated by white LEDs to indicate their availability. When the operator selects a control in a particular procedure, the control is illuminated by an amber LED to indicate that it is active. For example, the operator may be conducting a diagnostic procedure in which 2D images in grayscale are being acquired, but can also acquire the 2D images with colorflow indication of blood flow. The 2D button will be illuminated in amber at this time to show that the 2D mode is in use, and the Color button is illuminated in white to indicate that colorflow imaging is available in this procedure. If the operator then selects the Color button, colorflow imaging will commence and the Color button will change to an amber color to show the selection of the colorflow function.

As another example, the operator may be performing 3D imaging. If it is possible to switch immediately to 2D imaging, the 2D control will be illuminated in white to indicate the availability of the 2D imaging mode, and pressing the 2D control will change the system operation immediately to 2D imaging.

In the constructed control panel, different controls operate differently in response to different gestures or touches. The Color control is a simple on/off button, for example. When it is touched the first time it turns amber and is on; when it is touched again it turns back to white and is off but available for subsequent use. The 2D mode is a default mode and thus the 2D control is generally amber; it is rarely white. The four controls above the 2D button in FIG. 4, the Baseline, Scale/Focus, Depth and Gain controls, operate control functions which can be progressively increased or decreased. Repeatedly tapping the arrow at the top of the Gain control will progressively increase the gain of the signal amplifier in the system. Repeatedly tapping the arrow at the bottom of the Gain control will stepwise reduce the gain. The TGC controls to the right of the Gain control can be constructed to operate in a similar manner, or may be constructed as a series of individual lights and buttons. When the operator touches a different graphic dot on a TGC control, the touched dot will illuminate more brightly or in a different color, and the gain applied by that particular control will change in accordance with the location of the touched dot in the row of dots.

The touchpad 46 in the lower center of the control panel in FIGS. 4 and 6 can be operated in the manner of the trackball of a typical mechanical control panel. The operator can slide his or her finger around in the delineated touchpad area, causing a cursor or pointer on the display screen to be positionally controlled correspondingly. To select a screen function indicated by the cursor or pointer, the operator can touch one of the button areas immediately above the touchpad area, or can tap or double tap on the touchpad to select the indicated function.

FIG. 4 illustrates a constructed control panel of the present invention when all of the controls are illuminated and available. In practice, this is usually not the case. When the system operator selects an imaging mode or a specific imaging procedure or exam, as by selecting a mode or procedure from a list of selections on the display screen 62, the system will actuate and illuminate only those controls which are applicable to the selected mode or exam. Controls which have no use in the context of the selected mode or exam are not illuminated and are invisible to the operator. The operator will thus not be distracted by non-useful controls on a busy control panel. Instead, the operator's attention will be focused on only those controls which are useful for the current procedure.

The positions and the identified functions of the controls in the example of FIG. 4 are fixed, both by the fixed graphics behind the glass top and the fixed positions of the illuminated diffuser regions and light pipes behind them. With specific controls being in fixed positions, an operator will quickly become familiar with their positions and access them instinctively. An operator will not have to stop and wonder where a control may have been repositioned, which is often the case with scanned softkey displays. The operator soon becomes comfortable and efficient when using the control panel with its fixed control positions.

Figure 5:
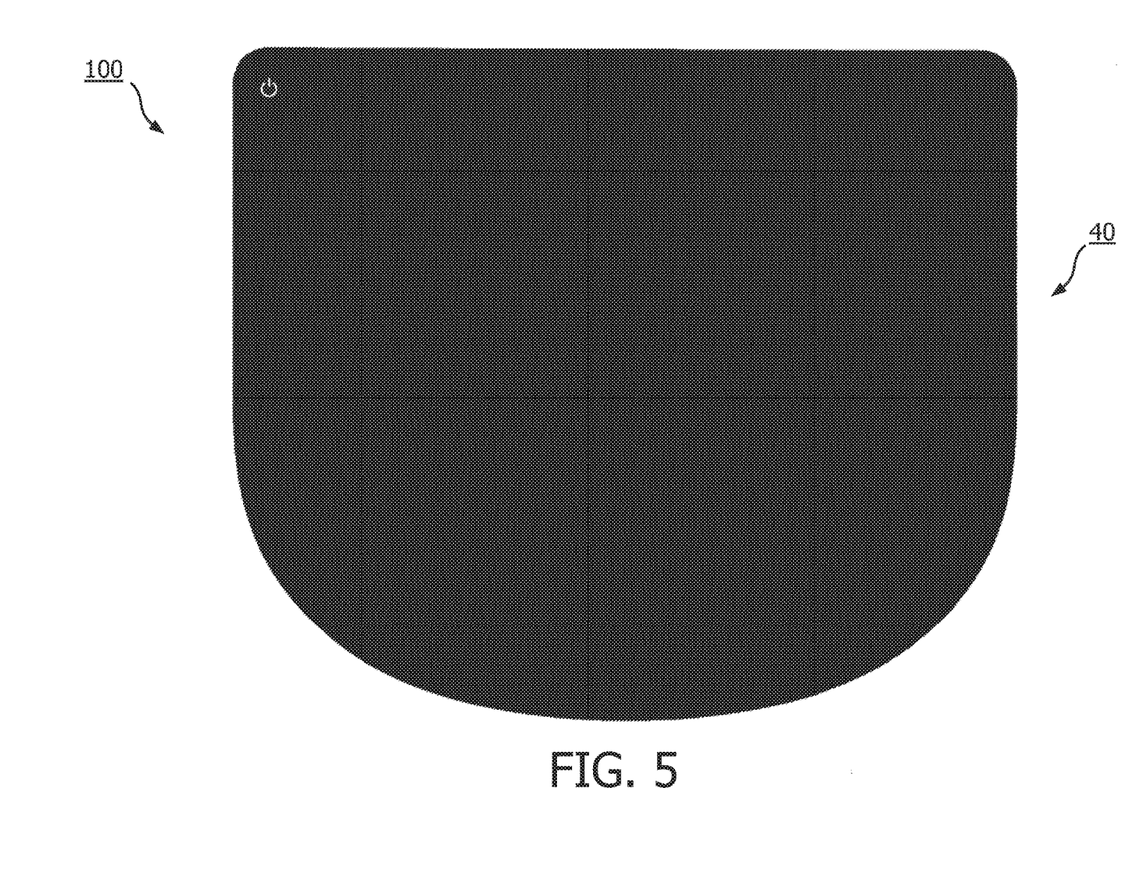
FIG. 5 illustrates the control panel of FIG. 4 when the controls have been inactivated for cleaning the control panel.

FIG. 5 illustrates the control panel of FIG. 4 when all of the ultrasound controls have been extinguished and turned off. This may be done by the on/off control 100 shown in the upper left-hand corner of the control panel. Alternatively, all of the controls may be de-activated and extinguished by a switch located on another part of the ultrasound system, such as on the display 62. An ultrasound system control panel can frequently need cleaning after being continuously touched by an operator during a series of exams. The control panel can also be marred by acoustic gel used by the operator to provide good acoustic coupling from the probe to the patient's body. If some of the controls were active during cleaning, the act of cleaning would unavoidably actuate controls on the panel, which is undesirable. An on/off control 100 is used to de-activate all of the controls on the panel, which is visually indicated by the lack of illumination of the controls. The control panel may then be cleaned without randomly actuating control panel controls. Cleaning the glass sheet forming the top of the control panel is easy and efficient, as the smooth top has no projections or crevices which trap debris and make cleaning difficult, as is the case with the typical mechanical control panel of knobs, buttons, and switches of the prior art. More comfortable and safer working conditions are thus afforded to both the operator and patient.

What is claimed is:

1. An ultrasound system comprising:
    an ultrasound probe for use in imaging;
    an image display screen; and
    a user control panel comprising:
        a surface and a plurality of user control graphics located on an underside of the surface at fixed positions, the control graphics being surrounded by an opaque color,
        a barrier layer on the underside of the surface, the barrier layer comprising a plurality of depressions that are below the control graphics and define illumination areas confined to the fixed positions of the user controls, the illumination areas comprising selectively illuminated light sources, and
        an illumination controller coupled to the light sources and configured to cause different groups of user control graphics to be illuminated for use during different operating modes in accordance with the need for the controls during a selected mode, with the illumination of unneeded user controls being extinguished such that the unneeded controls are substantially invisible to a user due to the opaque color.

2. The ultrasound system of claim 1, wherein the opaque color comprises black.

3. The ultrasound system of claim 2, wherein the surface is a surface of a glass sheet and the control graphics are screened onto the underside of the glass sheet.

4. The ultrasound system of claim 3, comprising a plurality of capacitive foils attached to the glass sheet at locations of control graphics.

5. The ultrasound system of claim 1, wherein each of the depressions contact a periphery of a corresponding user control above the barrier layer to confine light in a given depression to the user control above it.

6. The ultrasound system of claim 5, wherein the barrier layer comprises a diffuser frame and light pipes for the user controls.

7. The ultrasound system of claim 5, wherein the light sources comprise LEDs located in the depressions.

8. The ultrasound system of claim 7, wherein the illumination controller comprises a printed circuit board coupled to the barrier layer, and wherein the LEDs are electrically coupled to the printed circuit board to be controlled by the printed circuit board.

9. The ultrasound system of claim 7, wherein the light sources comprise LEDs of different colors located in the same depression, and wherein the different colors are used to illuminate the user control in accordance with a state of the function of the user control.

10. The ultrasound system of claim 9, wherein the state of the user control is available or active.

11. The ultrasound system of claim 1, further comprising a switch coupled to the user control panel, wherein the switch is actuated to extinguish the illumination of substantially all of the user controls.

12. The ultrasound system of claim 11, wherein actuation of the switch to extinguish the illumination further is configured to de-activate the users controls from their control functionality.

13. The ultrasound system of claim 11, wherein the switch is located at a position on the ultrasound system other than the surface of the control panel.

14. The ultrasound system of claim 12, wherein actuation of the switch to extinguish the illumination causes the user controls and their surrounding areas of the control panel to appear substantially invisible.

15. The ultrasound system of claim 1, wherein one of the user controls comprises a capacitive touchpad located forward of the center of the control panel toward a position of a user, a touch surface above the touchpad being flush with the surface of the control panel which is continuous with the touch surface of a majority of other user controls of the control panel.

* * * * *